United States Patent [19]

Sebag et al.

[11] Patent Number: 4,946,670

[45] Date of Patent: Aug. 7, 1990

[54] NEW POLYGYLCEROL ETHERS AND THEIR USE IN COSMETICS AND IN PHARMACY

[75] Inventors: Henri Sebag, Paris; Guy Vanlerberghe, Claye-Souilly, both of France

[73] Assignee: L'Oreal, Paris, France

[21] Appl. No.: 227,136

[22] Filed: Aug. 2, 1988

Related U.S. Application Data

[62] Division of Ser. No. 4,498, Jan. 20, 1987, Pat. No. 4,788,345.

[30] Foreign Application Priority Data

Jan. 27, 1986 [LU] Luxembourg ............... 86258

[51] Int. Cl.⁵ .............. A61K 7/021; A61K 7/075; A61K 7/48; A61K 47/10
[52] U.S. Cl. ........................... 424/47; 424/63; 424/64; 424/70; 424/DIG. 5; 514/772; 514/845; 514/846; 514/937; 514/938; 252/DIG. 13; 252/DIG. 1
[58] Field of Search .............. 424/70, 63, 64, 62, 424/47, DIG. 5; 8/405, 308, 315.1; 252/352, DIG. 1, DIG. 13; 514/772, 844, 845, 846, 847, 937, 938

[56] References Cited

U.S. PATENT DOCUMENTS 3,666,671 5/1972 Kalopissis et al. ............... 424/63 X
3,865,542 2/1975 Kalopissis et al. ............... 424/70 X
4,430,250 2/1984 Sebag et al. ...................... 424/64 X

FOREIGN PATENT DOCUMENTS 92239 9/1974 Japan .

Primary Examiner—Ellis P. Robinson
Assistant Examiner—Susan S. Rucker
Attorney, Agent, or Firm—Cushman, Darby & Cushman

[57] ABSTRACT

Mixture of compounds of general formula:

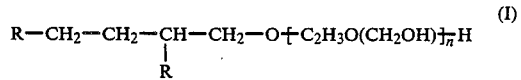

(I)

in which R denotes a saturated $C_{10}$–$C_{12}$ hydrocarbon radical, or mixture of such radicals, and n has a mean statistical value from 2 to 15, and preferably from 3 to 12.

These products are very well tolerated by the skin and the mucosa, and are advantageously used in cosmetic or pharmaceutical compositions.

19 Claims, No Drawings

POLYGLYCEROL ETHERS AND THEIR USE IN COSMETICS AND IN PHARMACY

This is a division of application Ser. No. 07/004,498, filed Jan. 20, 1987.

The invention relates to new nonionic surfactants, to the compositions containing them and to their use in cosmetics and in pharmacy.

These new surfactants are of the polyglycerol alkyl ether type. They show excellent biological tolerability; they can thus be used in compositions for treating the skin and the scalp.

The Applicant has already described, in U.S. Pat. No. 3,666,671, polyglycerol alkyl ethers and alkylaryl ethers of formula:

in which n denotes a number less than or equal to 10 and R denotes a linear or branched alkyl or alkenyl radical containing from 8 to 22 carbon atoms or alternatively a radical having from 8 to 30 carbon atoms and derived from lanolin alcohols, chiefly consisting of sterols (cholesterol, lanosterol) and, in smaller proportions, monohydric alcohols or 1,2-alkanediols which may be normal, iso- or anteiso-.

These are surfactants which have, depending on the number of carbon atoms in the radical, R, wetting, foaming, detergent or emulsifying properties.

The subject of the present invention is new polyglycerol ethers which are mainly non-foaming or weakly foaming surfactants which can be used as emulsifiers, as dispersants, as carriers or excipients or as additives in cosmetic and pharmaceutical compositions. Compared with the previous compounds mentioned above, these compounds show a substantial improvement as regards their properties in solution, in particular their emulsifying properties and their biological properties.

They can be represented by the following general formula (I):

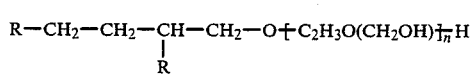

in which R denotes a saturated $C_{10}$ to $C_{12}$ hydrocarbon radical, or mixture of such radicals, and n denotes a mean statistical value from 2 to 15; R preferably denotes a decyl radical and n preferably denotes a mean statistical value from 3 to 12 and more especially from 3 to 8. The structure of the products of the invention is characterized by a substantial lipophilic block which contains at least 24 carbon atoms, combined with a portion which is more or less hydrophilic, depending on the number of units derived from glycerol. Despite the size of the lipophilic block, the products possess relatively low melting points, thereby avoiding the phenomena of crystallization in the compositions containing them.

These products show good emulsifying, dispersant or solubilizing properties, as well as good compatibility with the skin and the ocular mucosa. They are well tolerated in solution or in aqueous, oily or oleo-aqueous dispersion, and they also bring about a reduction in the attacking properties of other ionic or nonionic surfactants.

In effect, the compounds of formula (I), and more especially those for which n denotes 3 to 8, can be readily combined with surfactants such as foaming agents, in proportions from 5 to 50% by weight, and preferably from 10 to 30% by weight, of the weight of the foaming surfactants and, under these conditions, possess the advantage of reducing the attacking properties of the compositions containing them, in particular towards the ocular mucosa.

The subject of the invention is consequently also a non-attacking cosmetic composition for the skin and the ocular mucosa, containing one or more foaming surfactants and 5 to 50% by weight, relative to the weight of the foaming surfactants, of a compound of formula (I) in which n denotes a mean statistical value from 3 to 8.

The subject of the invention is also a process for reducing the attacking properties of foaming surfactants towards the skin or the ocular mucosa, characterized in that from 5 to 50% by weight, and preferably from 10 to 30% by weight, relative to the weight of the foaming surfactants, of a compound of formula (I) in which n denotes a mean statistical value from 3 to 8 is added to the foaming surfactants.

As a result of their high chemical stability and their nonionic nature which enables them to be combined readily with the different constituents customarily used in cosmetics, the compounds of formula (I) represent very advantageous products for the preparation of compositions for treating the skin, the scalp and the hair.

The products of formula (I) are obtained by two-stage reactions of an alcohol or a mixture of alcohols of formula (II):

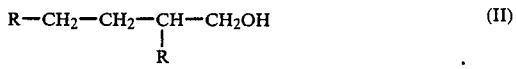

where R has the same meaning as above, with:
(i) an epihalohydrin as described in French Patent 1,477,048 or in U.S. Pat. No. 3,666,671, or alternatively with
(ii) t-butyl glycidyl ether as described in French Patent 2,027,585 or in U.S. Pat. No. 3,840,606.

When 1 mole of alcohol of formula (II) is reacted with n moles of glycerol epihalohydrin (n having the same meaning as above), the polyhalogenated intermediate compounds of formula:

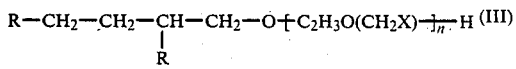

are obtained in which X denotes a halogen such as chlorine or bromine, and preferably chlorine.

During the polyaddition reaction of the epihalohydrin with the alcohol of formula (II), a mixture is formed of compounds all of which correspond to the general formula (III), but for which the number of moles of epihalohydrin bound can be greater than, equal to or less than the mean statistical value corresponding to the number of moles of epihalohydrin used for 1 mole of alcohol of formula (II). As a result, the formula (III) represents a mixture of compounds for which the set of values n is statistically distributed about a mean value corresponding to the number of moles of epihaloydrin used for 1 mole of hydroxyl compound.

The polyaddition reaction of epihalohydrin is performed in the presence of a Lewis acid catalyst such as boron trifluoride, stannic chlorideor antimony pentachloride, at a temperature of between 25° and 120° C., and preferably between 60° and 100° C.

The mixture of intermediate compounds of formula (III) is then "hydroxlated", that is to say the halogen atom X is replaced by an OH group, by reaction with an alkali metal salt of a carboxylic acid, and advantageously an alkali metal acetate, in stochiometric proportions or in slight excess with respect to the halogenated compound. This reaction is carried out in the presence of a solvent chosen from glycols or ethers thereof, such as ethylene glycol, diethylene glycol or dipropylene glycol, at a temperature of between 150° and 200° C.

When the alcohol of formula (II) is reacted with t-butyl glycidyl ether, the intermediate poly-t-butyloxy compounds of formula (IV):

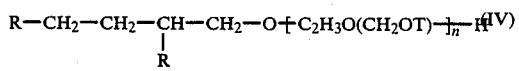

where T denotes a t-butyl radical, are obtained.

The reaction of the mixture of alcohols of formula (II) with t-butyl glycidyl ether is performed in the presence of a basic or acid catalyst. As basic catalysts, catalysts chosen from the group consisting of alkali metals, alkali metal hydroxides, alkali metal alcoholates and tertiary amines may be used. When an alkali metal catalyst is used, the reaction is performed at a temperature of 80° to 180° C.

As an acid catalyst, a catalyst chosen from the group consisting of Lewis acids, such as:

may be used, at a temperature below 120° C.

The intermediate poly-t-butyloxy compounds of formula (IV) are then hydrolysed in the presence of water and a strong acid which is used as catalyst. Among acids, methanesulphonic acid, p-toluenesulphonic acid or sulphoacetic acid may be mentioned in particular. The hydrolysis reaction is performed at a temperature of 50° to 120° C., and preferably from 90° to 100° C.

The hydroxylation of the intermediate compounds of formula (III), or the hydrolysis of the intermediate compounds of formula (IV), leads to a mixture of compounds of formula (I), containing a number of units derived from glycerol which is less than, equal to or greater then the value of n, which represents a mean statistical value.

The products which form the subject of the invention consist of mixtures of polyglycerol ethers (I) as obtained after the hydroxylation or hydrolysis reactions, without separation of the different homologues, this separation always being tedious and expensive.

The products of the invention generally take the form of thick liquids or of pastes which are soluble in oils for values of n equal to or less than approximately 7 and dispersible in water for values of n equal to or greater than approximately 5. The compounds for which n is between 5 and 7 can be both soluble in oils and dispersible in water.

The subject of the invention is also compositions, and especially cosmetic and pharmaceutical compositions, containing the mixtures of compounds of formula (I). These compositions can be aqueous compositions or oily compositions in the form of liquids, gels or waxes, or alternatively oleo-aqueous compositions in the form of water-in-oil or oil-in-water emulsion, or alternatively aqueous alcoholic solutions. The compositions can, in addition, take the form of aerosols.

The aqueous or oily compositions, in liquid or gel form, are, for example, shampoos, make-up removal lotions for the eyes or the face, foaming oils for the hair or the skin, products for the bath or shower and, generally, toilet products.

The compositions in wax form are sticks for application to the lips, designed either to colour them or to prevent chapping, or make-up products for the eyes, or make-up or make-up foundations for the face.

When the compositions according to the invention take the form of a water-in-oil or oil-in-water emulsion, the emulsifying agent can consist exclusively of the compound or compounds (I) according to the invention. The compounds of formula (I) can also be combined with any other traditional emulsifier such as, for example, polyoxyethylenated fatty acids or fatty alcohols, polyglycerol alkyl ethers, polyoxyethylenated sorbitan esters, or amine or polyvalent metal salts of fatty acids.

The fatty substances forming the fatty phase of the emulsions are oils or waxes. Among oils, there may be mentioned mineral oils such as liquid paraffin; animal oils such as whale oil, seal oil, halibut-liver oil, cod oil, tuna oil, tallow oil and mink oil; and vegetable oils such as almond oil, groundnut oil, wheat-germ oil, corn oil, olive oil, jojoba oil, sesame oil and sunflower oil.

Among waxes, there may be mentioned sipol wax, lanolin wax, beeswax, candelilla wax, microcrystaline wax, carauba wax, spermaceti, cocoa butter, shea butter, silicone waxes and hydrogenated oils which are solid at 25° C.

The oils or waxes can also be chosen from the esters formed by saturated or unsaturated $C_{12}$ to $C_{22}$ fatty acids with lower alcohols or polyols such as isopropanol, glycol or glycerol, or with saturated or unsaturated linear or branched $C_8$ to $C_{22}$ fatty alcohols, or with $C_{10}$–$C_{22}$ 1,2-alkanediols.

As fatty substances, vaseline, paraffin, lanolin, hydrogenated lanolin, acetylated lanolin and silicone oils may also be mentioned.

When the compositions of the invention take the form of a solution or aqueous dispersion, or an emulsion, or the form of an oily composition, to constitute washing products for skin care and hair care, the compounds of formula (I) can be used alone or with other surfactants. The compounds of formula (I) can be used as emulsifiers, cleaning agents, dipersants, carriers or excipients, or superfatting agents, and they also possess the advantage of reducing the toxicity of the surfactants with which they are combined, in particular towards the mucosa. In this case, from 5 to 50% by weight of compounds of formula I, relative to the total weight of the surfactants, is preferably used.

The compositions according to the invention can also be dispersions of lipids in water, and can take the form of dispersions of lamellar phases or vesicular dispersions. In these compositions, the compounds of formula (I) can be combined with neutral lipids such as chlolesterol, or with charged lipids such as chlolesterol sulphate, cholesterol phosphate, ditetradecyl phosphate of dihexadecyl phosphate, in acid form or in the form of sodium or potassium salt.

The compounds according to the invention can contain amounts of products of formula (I) between 0.1 and 80% by weight, and more generally from 0.5 to 25% by weight.

In the compositions according to the invention, the products or mixtures of compounds (I) can be combined with other surfactants, with ionic or nonionic lipids, with ionic or nonionic natural or synthetic polymers, with oils or waxes, with proteins hydrolysed to a greater or lesser extent, with thickeners, with pearlescent agents, with emollients, with colourings, with reducing or oxidizing agents, with preservatives, with perfumes, with inorganic or organic acids or bases, with pigments, with solvents, with propellants or with pharmaceutical or parapharmaceutical active products.

The subject of the invention is also a process for treating the skin, the scalp or the hair with a composition containing a mixture of compounds of formula (I). P Other subjects of the invention will emerge on reading the examples.

EXAMPLE 1

Preparation of a mixture of compounds of general formula (I) in which:
$\underline{R}$ denotes a decyl radical and
$\overline{n}$ the mean statistical value 3.

To 354 g (1 mole) of 2-decyltetradecanol, sold under the name "Isofol 24" by Condea, 1.6 ml of $BF_3$ etherate is added, followed, at 50/55° C. in the course of 1 hour 40 minutes, by 277.5 g (3 moles) of epichlorohydrin.

The mixture is then left for approximately 15 minutes while stirring at the same temperature.

A brown viscous liquid is thereby obtained.

630 g of dipropylene glycol (DPG), 297 g (3.03 mole) of potassium acetate and 1.3 g of sodium hypophosphite are added to 631.5 g of polychlorinated derivatives (3 equivalents of chlorine) thereby obtained. The reaction mixture is then heated to 180° C. for 5 hours.

The extent of reaction, determined by assaying the unreacted potassium acetate or the amount of inorganic chlorine formed, is greater than 96%.

The inorganic salts are separated by filtration and rinsed with 100 ml of DPG. The solvent is removed by heating under reduced pressure. The residue is then taken up with 600 ml of absolute ethanol in the presence of sodium methylate (30 meq).

After 24 hours at room temperature, the precipitated mineral salts are filtered off and the solvents evaporated off under reduced pressure.

A viscous, amber coloured liquid product, which is insoluble in water and soluble in liquid paraffin, is thereby obtained.

The cloud point, measured at 5% in an aqueous solution containing 25% of diethylene glycol butyl ether (DGB) is 70° C.

EXAMPLE 2

Preparation of a mixture of compounds of general formula (I) in which:
$\underline{R}$ denotes a decyl radical and
$\overline{n}$ the mean statistical value 5.

To 70.8 g (0.2 mole) of 2-decyltetradecanol, 0.4 ml of $BF_3$ etherate is added, followed, at 50°/55° C. in the course of 1 hour 15 minutes, by 92.5 g (1 mole) of epichlorohydrin.

After 30 minutes' stirring at 50° C., it is verified by assay that all the epoxide has reacted.

The mixture of polychlorinated derivatives thereby obtained is taken up in 163 g of diethylene glycol (DEG). 84.5 g of sodium acetate (1.03 mole) are then added, and the mixture is then heated to 180°–185° C. under an atmosphere of nitrogen for 4 hours. The inorganic salts are filtered off and the DEG distilled off under reduced pressure. The residual mass is taken up with 140 g of absolute ethanol in the presence of sodium methylate (7 meq).

After the mixture has been left standing overnight at room temperature, a slight precipitate is separated by filtration and the solvents are distilled off under reduced pressure.

A brown product, which takes the form of a soft paste which is soluble in liquid paraffin, is thereby obtained.

The cloud point, at 5% in an aqueous solution containing 25% of DGB, is 90° C.

EXAMPLE 3

Preparation of a mixture of compounds of general formula (I) in which:
$\underline{R}$ denotes a decyl radical and
$\overline{n}$ the mean statistical value 8.

To 265.5 g (0.75 mole) of 2-decyltetradecanol, 2 ml of $BF_3$ etherate are added, followed, in the course of 2 hours 20 minutes at 55° C., by 555 g (6 moles) of epichlorohydrin.

When all the epoxide has reacted, the reaction mass is taken up with 820 g of DEG. 497 g (6.06 mole) of sodium acetate and 1.6 g of sodium hypophosphite are added, and the mixture is then heated under an atmosphere of nitrogen to 180° C. for 5 hours. The inorganic salts are then filtered off, and then rinsed with DEG. The solvent is driven off under reduced pressure.

The residue, taken up in 700 g of absolute ethanol in the presence of 6.3 g of a methanolic solution of sodium methylate (36 meq), is left overnight at room temperature.

After the precipitate has been filtered off and the solvents have been distilled off, a soft, amber coloured paste, which is dispersible in water, is obtained.

The cloud point in DGB is above 100° C.

EXAMPLE 4

Preparation of a mixture of compounds of general formula (I) in which:
$\underline{R}$ denotes a decyl radical and
$\overline{n}$ the mean statistical value 12.

To 17.7 g of 2-decyltetradecanol (0.05 mole), 0.25 ml of $SnCl_4$ are added followed, dropwise at 60° C. in the course of 2 hours 10 minutes, by 55.5 g of epichlorohydrin (0.6 mole).

After the mixture is cooled, a very pale coloured viscous liquid is obtained.

The mixture of polychlorinated derivatives is washed at 95° C. with 75 g of a 20% strength aqueous solution of $Na_2CO_3$.

After decantation and drying, 61 g of the residue thereby obtained (0.5 equivalents of chlorine) are taken up with 60 g of DEG. 41 g of sodium acetate (0.5 mole) and 0.12 g of sodium hypophosphite are added and the mixture is heated under an atmosphere of nitrogen to 180° C. for 4 hours 30 minutes.

The extent of reaction is then 98%.

After the inorganic solvent have been filtered off and the solvents distilled off under reduced pressure, and ethanolysis, as in the above examples, a brown paste is obtained which is almost soluble in water, with thickening.

APPLICATION EXAMPLES

EXAMPLE A1

| Oxidation dyeing composition for the hair | |
|---|---|
| Mixture of compounds prepared according to Example 1 | 10 g |
| Mixture of compounds prepared according to Example 3 | 5 g |
| Coconut fatty acid diethanolamides | 13 g |
| Ethyl alcohol | 5 g |
| Propylene glycol | 12 g |
| Ethylenediaminetetraacetic acid | 0.2 g |
| 2-Butoxyethanol | 6 g |
| 20% Strength ammonia solution | 10 g |
| Resorcinol | 0.6 g |
| m-Aminophenol | 0.22 g |
| p-Aminophenol | 0.23 g |
| Ammonium thiolactate | 0.80 g |
| Water q.s. | 100 g |

This composition is mixed at the time of use with an equal volume of 6% strength hydrogen peroxide. A transparent gel is obtained which is applied on grey hair for 30 minutes.

After rinsing and washing, the hair is dyed an iridescent blonde. The hair is shiny and has body.

EXAMPLE A2

| Composition for bleaching the hair | |
|---|---|
| Mixture of compounds prepared according to Example 1 | 12 g |
| Mixture of compounds prepared according to Example 3 | 6 g |
| Coconut fatty acid diethanolamides | 11 g |
| Ethyl alcohol | 4.5 g |
| Propylene glycol | 12.5 g |
| 2-Butoxyethanol | 6 g |
| Ethylenediaminetetraacetic acid | 0.2 g |
| 20% Strength ammonia solution | 12 g |
| Water q.s. | 100 g |

This composition is mixed with an equal volume of 6% strength hydrogen peroxide to form a gel, and is applied on chestnut coloured hair for 40 minutes.

After rinsing and shampooing, the hair is bleached blonde. The hair is lively, shiny and has body.

EXAMPLE B1

| Demulcent cream for the face: Water-in-oil emulsion | |
|---|---|
| Mixture of compounds of Example 1 | 11 g |
| Paraffin oil | 10.7 g |
| Volatile silicone oil | 10.7 g |
| Modified hectorite sold under the name MYGLYOL GEL by DYNAMIT NOBEL | 5 g |
| Magnesium sulphate | 2 g |
| Glycerin | 3 g |
| Water q.s. | 100 g |

EXAMPLE B2

| Skin cream: Oil-in-water emulsion | |
|---|---|
| Mixture of compounds of Example 3 | 10 g |
| Paraffin oil | 40 g |
| Water q.s. | 100 g |

EXAMPLE C

| Oil for the body, to be rinsed | |
|---|---|
| Mixture of compounds of example 2 | 15 g |
| Coconut fatty acid diethanolamides | 8.75 g |
| Polyethoxylated $C_{12}$–$C_{14}$ alcohols containing 2.2 ethoxy units | 8.75 g |
| Cationic surfactant of formula: | |

$$R-CONH-(CH_2)_2-\overset{\oplus}{N}H-(CH_2)_2-NH-COR$$
$$\underset{CH_2CH_2OH}{|} \quad CH_3CHOH-COO^{\ominus}$$

| | |
|---|---|
| R = mixture of unsaturated $C_{16}$–$C_{18}$ radicals, sold under the name EMPIGEN FKH by MARCHON | 2.5 g |
| Liquid paraffin | 25 g |
| Antioxidants | 0.1 g |
| Propyl p-hydroxybenzoate | 0.2 g |
| Rapeseed oil q.s. | 100 g |

This oil is used for washing the skin.
After rinsing, the skin is smooth.

EXAMPLE D

| Shampoo | |
|---|---|
| Mixture of compounds of Example 2 | 3 g |
| Polyglycerol alkyl ethers (containing 10 to 12 carbon atoms in the alkyl portion and 4 units derived from glycerol) | 10 g |
| Copolymer of dimethyldiallylammonium chloride and acrylamide, sold containing 8% AS (active substance) by MERCK under the name MERQUAT 550 | 7.5 g |
| Perfume, colouring, preservative q.s. | |
| Water q.s. | 100 g |
| The pH is adjusted to 7. | |

.When applied on soiled hair, this composition develops a gentle and creamy foam which is easily rinsed. The wet hair is soft and easy to disentangle.
The dry hair is shiny and soft.

EXAMPLE E

| Body milk | |
|---|---|
| Polyoxyethylene/polydodecyl glycol copolymer sold under the name "ELFACOS ST9" by AKZO | 2.5 g |
| Mixture of compounds of Example 1 | 2.5 g |
| Hectorite modified with dimethyldistearyl-ammonium chloride, sold under the name "BENTONE 38" by NL INDUSTRIES | 1.0 g |
| Volatile silicone | 8.0 g |
| Cetyl/stearyl ethylhexanoate having low freezing point (of the palmiped feather grease type), sold under the name "PUR-CELLIN OIL" | 6.0 g |
| Sunflower oil | 6.0 g |
| Preservatives | 0.35 g |
| Glycerin | 5.0 g |
| Demineralized water q.s. | 100 g |

EXAMPLE F

| Night care cream for dry skin | |
|---|---|
| Polyoxyethylene/polydodecyl glycol copolymer sold under the name "ELFACOS ST9" by AKZO | 2.5 g |
| Mixture of compounds of Example 1 | 2.5 g |
| Dodecanediol/polyethylene glycol (45) ether sold under the name "ELFACOS C 26" by AKZO | 0.8 g |

| Night care cream for dry skin | |
|---|---|
| Hectorite modified with dimethyldistearyl-ammonium chloride, sold under the name "BENTONE 38" by NL INDUSTRIES | 1.0 g |
| White vaseline | 6.0 g |
| Grape pip oil | 6.0 g |
| Vitamin F | 2.0 g |
| Light liquid paraffin | 6.0 g |
| Preservatives | 0.2 g |
| Glycerin | 5.0 g |
| Demineralized water q.s. | 100 g |

EXAMPLE G

| Washing oil | |
|---|---|
| Mixture of compounds of Example 2 | 3.0 g |
| Mixture of monoisopropanolamine lauryl ether sulphate and coconut diethanolamides, sold under the name "TEXAPON WW99" by HENKEL | 30 g |
| Liquid paraffin | 25 g |
| Colouring, perfume, preservative q.s. | |
| Rapeseed oil q.s. | 100 g |

EXAMPLE H

| Fluid milk for the face | |
|---|---|
| Mixture of compounds of Example 3 | 3.1 g |
| Cholesterol | 1.65 g |
| Dicetyl phosphate (acid) | 0.25 g |
| Water q.s. | 100 g |

We claim:

1. A cosmetic composition for the treatment of the skin, scalp or hair comprising, in a cosmetically acceptable vehicle, in an amount effective to treat the skin, scalp or hair, a mixture of compounds having the formula

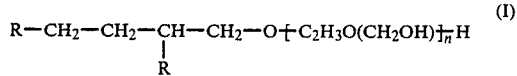

wherein
R represents a saturated hydrocarbon radical, or a mixture of saturated hydrocarbon radicals, having 10 to 12 carbon atoms, and
n represents a mean statistical value of 2 to 15.

2. The cosmetic composition of claim 1 which also contains at least one cosmetic adjuvant selected from the group consisting of an anionic, cationic, nonionic, amphoteric and zwitterionic surfactant; an ionic or nonionic lipid; an ionic or nonionic natural or synthetic polymer; an oil; a wax; a protein; a thickener; a pearlescent agent; an emollient; a coloring; a preservative; a perfume; an acid; a base; a pigment; a solvent; and a propellant.

3. The cosmetic composition of claim 1 wherein said mixture of compounds of formula (I) is present in an amount ranging from 0.1 to 80 percent by weight.

4. The cosmetic composition of claim 1 wherein said mixture of compounds of formula (I) is present in an amount ranging from 0.5 to 25 percent by weight.

5. The cosmetic composition of claim 1 in the form of an aqueous or aqueous alcoholic composition, an oily composition, an oil-in-water emulsion, a water-in-oil emulsion, a gel, a wax or an aerosol.

6. The cosmetic composition of claim 1 in the form of an oil-in-water emulsion or a water-in-oil emulsion, said composition also containing an oil or wax.

7. The cosmetic composition of claim 6 which also contains an emulsifier other than the mixture of compounds of formula (I).

8. The cosmetic composition of claim 1 in the form of a shampoo, a make-up removal lotion for the eyes or face, or a bath or shower product.

9. The cosmetic composition of claim 1 in the form of an oily composition, said oily composition being a make-up removal lotion for the eyes or face or a foaming oil for the hair or skin.

10. The cosmetic composition of claim 1 comprising a dipersion of lipids in the water and being in the form of a dispersion of lamellar phases or a vescular dispersion.

11. The cosmetic composition of claim 10 wherein the compounds of formula (I) are combind with a lipid selected from the group consisting of a neutral lipid and a charged lipid.

12. The cosmetic composition of claim 11 wherein said neutral lipid is cholesterol.

13. The cosmetic composition of claim 11 wherein said charged lipid is selected from the group consisting of cholesterol sulphate, chlolesterol phosphate, ditetradecyl phosphate and dihexadecyl phosphate, in acid form or in the form of a sodium or potassium salt thereof.

14. The cosmetic composition of claim 1 in the form of a stick for application to the lips, a make-up product for the eyes or a make-up product for the face.

15. A cosmetic composition which is non-aggressive towards the skin and ocular mucosa comprising at least one foaming surfactant and 5 to 50 percent by weight, based on the weight of said foaming surfactant, of a compound having the formula

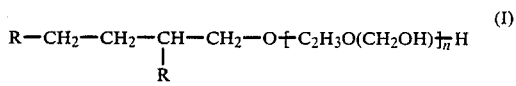

wherein
R represents a saturated hydrocarbon or a mixture of saturated hydrocarbons, having from 10 to 12 carbon atoms, and
n has a mean statistical value ranging from 3 to 12.

16. A pharmaceutical composition for the treatment of the skin, scalp or hair comprising in a pharmaceutically acceptable vehicle, in an amount effective to treat the skin, scalp or hair, a mixture of compounds having the formula

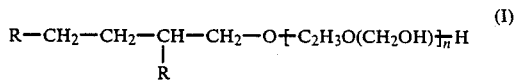

wherein
R represents a saturated hydrocarbon, or a mixture of saturated hydrocarbons, having 10 to 12 carbon atoms, and
n has a mean statistical value ranging from 2 to 15.

17. The pharmaceutical composition of claim 16 which also contains a pharmaceutically or parapharmaceutically active product.

18. A process for treating the skin, scalp or hair comprising applying to said skin, scalp or hair in an amount effective to treat said skin, scalp or hair the composition of claim 1.

19. A process for reducing the aggressiveness of a foaming surfactant towards the skin or ocular mucosa comprising adding to said foaming surfactant from 5 to 50 weight percent, based on the weight of said foaming surfactant, of a mixture of compounds having the formula

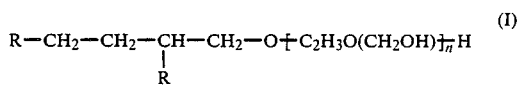

wherein
R represents a saturated hydrocarbon, or a mixture of saturated hydrocarbons, having from 10 to 12 carbon atoms, and
n has a mean statistical value ranging from 3 to 8.

* * * * *